(12) United States Patent
Raab et al.

(10) Patent No.: US 9,463,284 B2
(45) Date of Patent: Oct. 11, 2016

(54) DOSE DISPLAY MECHANISM FOR DRUG DELIVERY DEVICE WITH FIRST AND SECOND WINDOWS AND SCALES

(75) Inventors: Steffen Raab, Frankfurt am Main (DE); Sandra Arnhold, Büttelborn (DE)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 1153 days.

(21) Appl. No.: 13/509,600

(22) PCT Filed: Dec. 1, 2010

(86) PCT No.: PCT/EP2010/068591
§ 371 (c)(1),
(2), (4) Date: Sep. 24, 2012

(87) PCT Pub. No.: WO2011/067267
PCT Pub. Date: Jun. 9, 2011

(65) Prior Publication Data
US 2013/0016105 A1  Jan. 17, 2013

(30) Foreign Application Priority Data

Dec. 2, 2009  (EP) .................................. 09177682

(51) Int. Cl.
*A61M 5/315* (2006.01)
*G06M 1/22* (2006.01)
*A61M 5/31* (2006.01)

(52) U.S. Cl.
CPC ............ *A61M 5/31551* (2013.01); *G06M 1/22* (2013.01); *A61M 2005/3125* (2013.01); *A61M 2005/3126* (2013.01); *A61M 2205/583* (2013.01); *A61M 2205/586* (2013.01)

(58) Field of Classification Search
CPC ......... A61M 25/0631; A61M 5/3216; A61M 5/158; A61M 25/0074; A61M 25/0111; A61M 5/315; A61M 5/31; A61B 2018/00946; A61B 2018/0091; A61B 2018/00952
See application file for complete search history.

(56) References Cited

U.S. PATENT DOCUMENTS 2,432,605 A  *  12/1947  Barach ............... A61M 5/31511
                                                    116/227
2,515,956 A  *  7/1950  Greenberg ........ A61M 5/31531
                                                   417/DIG. 1

(Continued)

FOREIGN PATENT DOCUMENTS

EP       1642607       4/2006
WO     2004/069314     8/2004

(Continued)

OTHER PUBLICATIONS

International Preliminary Report on Patentability for Int. App. No. PCT/EP2010/068591, mailed Jun. 14, 2012.

(Continued)

*Primary Examiner* — Bhisma Mehta
*Assistant Examiner* — Matthew A Engel
(74) *Attorney, Agent, or Firm* — McDonnell Boehnen Hulbert & Berghoff LLP

(57) ABSTRACT

The present invention relates to a drug delivery device, in particular to the dose display mechanism of a drug delivery device comprising: a housing of substantially tubular shape and having at least a first dose displaying window, a dose setting dial rotatably arranged in the housing) and comprising a first and a second helical dose indicating scale on its peripheral surface, wherein the information contents of the first dose indicating scale and the second dose indicating scale are arranged in different orientations.

12 Claims, 5 Drawing Sheets

(56) References Cited

U.S. PATENT DOCUMENTS

| | | | | |
|---|---|---|---|---|
| 2,658,511 A * | 11/1953 | Furnell | A61B 5/1405 | 604/218 |
| 4,357,971 A * | 11/1982 | Friedman | A61M 5/1782 | 141/95 |
| 4,475,905 A * | 10/1984 | Himmelstrup | A61M 5/31551 | 604/208 |
| 4,865,591 A * | 9/1989 | Sams | A61M 5/31553 | 222/287 |
| 5,092,842 A * | 3/1992 | Bechtold | A61M 5/20 | 604/135 |
| 5,226,895 A * | 7/1993 | Harris | A61J 1/1406 | 604/208 |
| 5,226,896 A * | 7/1993 | Harris | A61M 5/31551 | 604/208 |
| 5,279,585 A * | 1/1994 | Balkwill | A61M 5/3158 | 222/309 |
| 5,279,586 A * | 1/1994 | Balkwill | A61M 5/3158 | 222/309 |
| 5,295,976 A * | 3/1994 | Harris | A61M 5/31551 | 604/208 |
| 5,308,340 A * | 5/1994 | Harris | A61J 1/1406 | 604/208 |
| 5,320,609 A * | 6/1994 | Haber | A61M 5/2033 | 604/135 |
| 5,354,285 A * | 10/1994 | Mazurik | A61M 5/31511 | 604/191 |
| 5,376,081 A * | 12/1994 | Sapienza | A61M 5/3129 | 604/186 |
| 5,482,163 A * | 1/1996 | Hoffman | A61J 7/04 | 116/309 |
| 5,582,598 A * | 12/1996 | Chanoch | A61M 5/31551 | 222/309 |
| 5,693,027 A * | 12/1997 | Hansen | A61M 5/24 | 604/200 |
| 5,728,074 A * | 3/1998 | Castellano | G06F 19/3468 | 600/309 |
| 5,823,346 A * | 10/1998 | Weiner | A61J 7/04 | 206/459.1 |
| 6,764,469 B2 * | 7/2004 | Broselow | A61M 5/31525 | 604/207 |
| 6,899,698 B2 * | 5/2005 | Sams | A61M 5/20 | 604/211 |
| 7,976,506 B2 * | 7/2011 | Vitullo | A61M 5/28 | 604/187 |
| 8,001,963 B2 * | 8/2011 | Giroux | A61M 15/08 | 128/200.14 |
| 8,202,255 B2 * | 6/2012 | Saiki | A61M 5/31551 | 604/181 |
| 8,298,194 B2 * | 10/2012 | Moller | A61M 5/24 | 604/181 |
| 8,348,904 B2 * | 1/2013 | Petersen | A61M 5/24 | 604/207 |
| 9,022,991 B2 * | 5/2015 | Moeller | A61M 5/24 | 604/208 |
| 9,186,459 B2 * | 11/2015 | Bechmann | A61M 5/2033 | |
| 2002/0020654 A1 * | 2/2002 | Eilersen | A61M 5/24 | 206/570 |
| 2002/0022821 A1 * | 2/2002 | Eilersen | G06K 7/10 | 604/404 |
| 2002/0165500 A1 * | 11/2002 | Bechtold | A61M 5/2033 | 604/209 |
| 2003/0050609 A1 * | 3/2003 | Sams | A61M 5/20 | 604/208 |
| 2003/0120222 A1 * | 6/2003 | Vaillancourt | A61M 5/321 | 604/263 |
| 2005/0183982 A1 * | 8/2005 | Giewercer | A61J 7/04 | 206/534 |
| 2006/0258988 A1 * | 11/2006 | Keitel | A61M 5/31551 | 604/181 |
| 2008/0051692 A1 * | 2/2008 | Petersen | A61N 1/303 | 604/20 |
| 2008/0171995 A1 * | 7/2008 | Vitullo | A61M 5/28 | 604/187 |
| 2009/0062728 A1 * | 3/2009 | Woo | A61M 5/1723 | 604/66 |
| 2009/0062730 A1 * | 3/2009 | Woo | A61M 5/1723 | 604/66 |
| 2009/0264828 A1 | 10/2009 | Dette et al. | | |
| 2011/0313396 A1 * | 12/2011 | Chanoch | A61M 5/31561 | 604/506 |
| 2011/0313397 A1 * | 12/2011 | Gold | A61M 5/31551 | 604/506 |
| 2012/0071834 A1 * | 3/2012 | Harms | A61M 5/3129 | 604/189 |
| 2012/0089098 A1 * | 4/2012 | Boyd | A61M 5/24 | 604/189 |
| 2012/0101445 A1 * | 4/2012 | Jansen | A61M 5/24 | 604/189 |
| 2012/0210924 A1 * | 8/2012 | Kawai | D05B 7/06 | 112/254 |
| 2012/0232517 A1 * | 9/2012 | Saiki | A61M 5/31551 | 604/500 |
| 2012/0253288 A1 * | 10/2012 | Dasbach | A61J 7/04 | 604/189 |
| 2012/0310172 A1 * | 12/2012 | MacDonald | A61M 5/31525 | 604/207 |
| 2012/0330228 A1 * | 12/2012 | Day | A61M 5/14244 | 604/82 |
| 2013/0072897 A1 * | 3/2013 | Day | A61M 5/1452 | 604/500 |
| 2013/0079708 A1 * | 3/2013 | Wimpenny | A61M 5/002 | 604/65 |
| 2013/0096511 A1 * | 4/2013 | MacArthur | A61J 1/06 | 604/189 |
| 2013/0131601 A1 * | 5/2013 | Pommereau | A61M 5/3129 | 604/189 |
| 2013/0226095 A1 * | 8/2013 | Dasbach | A61J 7/04 | 604/189 |
| 2014/0221974 A1 * | 8/2014 | Bechmann | A61M 5/2033 | 604/506 |
| 2014/0323974 A1 * | 10/2014 | Roervig | A61M 5/24 | 604/189 |

FOREIGN PATENT DOCUMENTS

| | | |
|---|---|---|
| WO | 2007/067889 | 6/2007 |
| WO | 2007/099093 | 9/2007 |
| WO | 2010/003569 | 1/2010 |

OTHER PUBLICATIONS

European Search Report for EP App. No. 09177682, completed Apr. 23, 2010.

International Search Report for Int. App. No. PCT/EP2010/068591, completed Feb. 28, 2011.

Japanese Office Action for JP App. No. 2012-541476, dated Mar. 31, 2015.

* cited by examiner

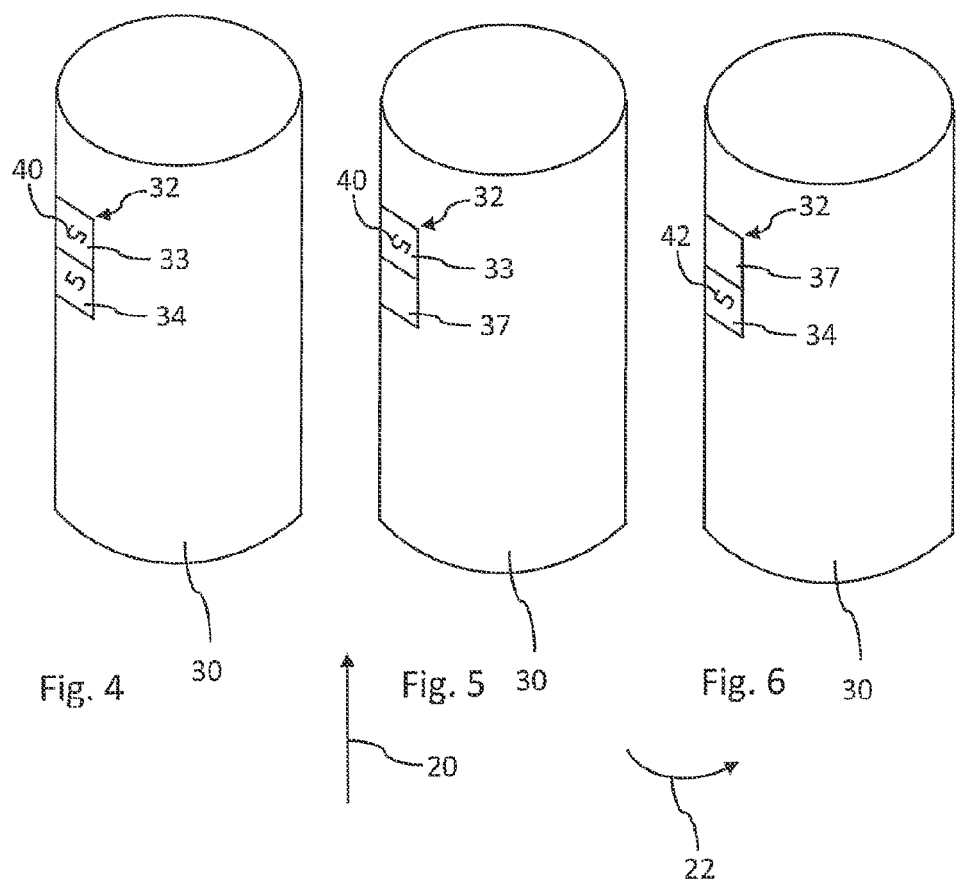

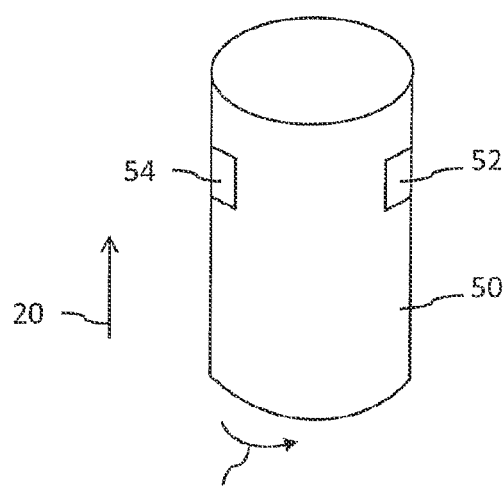
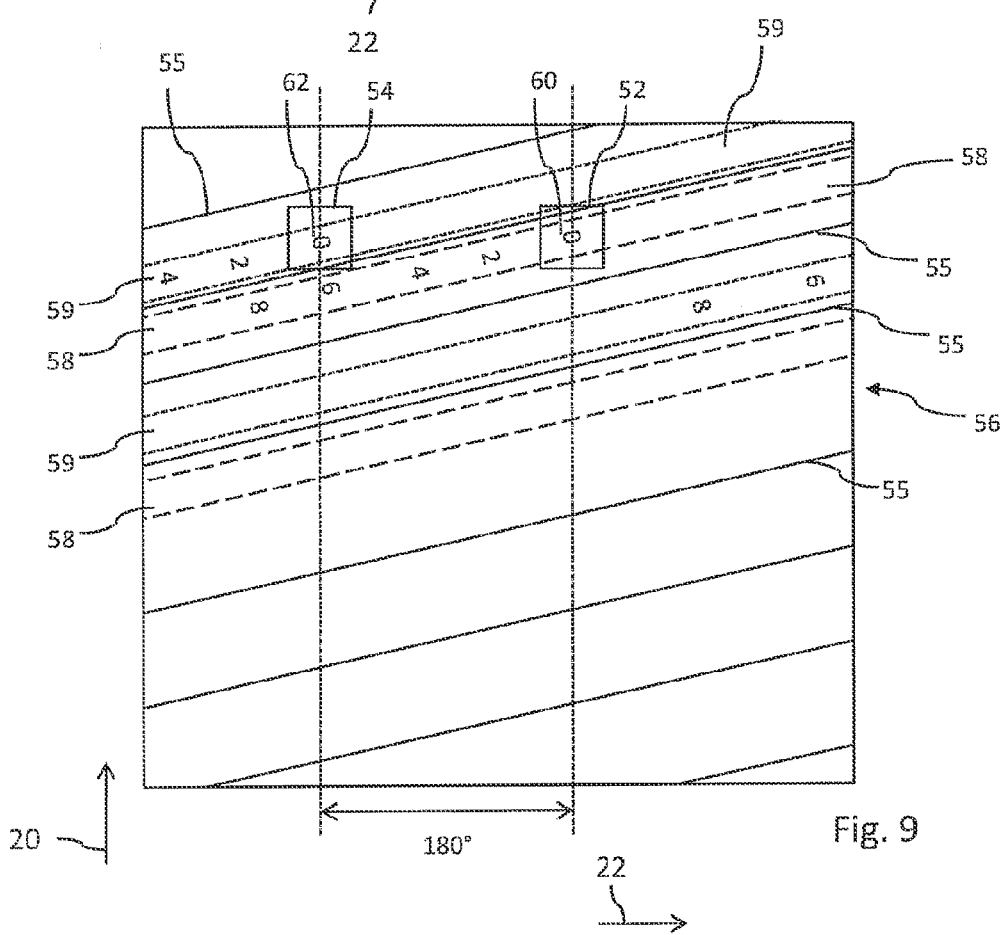
Fig. 8
Fig. 9

DOSE DISPLAY MECHANISM FOR DRUG DELIVERY DEVICE WITH FIRST AND SECOND WINDOWS AND SCALES

CROSS REFERENCE TO RELATED APPLICATIONS

The present application is a U.S. National Phase Application pursuant to 35 U.S.C. §371 of International Application No. PCT/EP2010/068591 filed Dec. 1, 2010, which claims priority to European Patent Application No. 09177682.3 filed on Dec. 2, 2009. The entire disclosure contents of these applications are herewith incorporated by reference into the present application.

FIELD OF THE INVENTION

This invention relates to a dose display mechanism for a drug delivery device that allows a user to select multiple doses of an injectable medicinal product and for the dispensing of a set dose and applying said medicinal product to a patient, preferably by injection. In particular, the invention relates to such devices, which are handled by the patients themselves and which are therefore adapted for self-administration.

BACKGROUND

Drug delivery devices allowing for multiple dosing of a required dosage of a liquid medicinal product, such as liquid drugs, and further providing administration of the liquid to a patient, are as such well-known in the art. Generally, such devices have substantially the same purpose as that of an ordinary syringe.

Pen-type injectors of this kind have to meet a number of user specific requirements. For instance in case of those with diabetes, many users will be physically infirm and may also have impaired vision. Therefore, these devices need to be robust in construction, yet easy to use, both in terms of the manipulation of the parts and understanding by a user of its operation. Further, the dose setting must be easy and unambiguous and where the device is to be disposable rather than reusable, the device should be inexpensive to manufacture and easy to dispose. In order to meet these requirements, the number of parts and steps required to assemble the device and an overall number of material types the device is made from have to be kept to a minimum.

Document EP 1 642 607 A1 for instance discloses a dose display mechanism consisting of a dose setting dial and a counter ring each displaying indices on their outer circumference arranged such that a two-indices representation of the selected dose can be displayed. The dose setting dial and the counter ring comprise single digits that are visible through a display window of a housing.

The digits are displayed in a readable orientation when the drug delivery device is oriented substantially horizontally. Since most drug delivery devices are designed for right-handed users, the digits are displayed in a correct and upright orientation when from a user's point of view, the distal end section of the device points to the left and when the proximal end section of the device points to the right hand side.

Such a display orientation is particularly applicable, where the user or patient holds the housing of the drug delivery device with his left hand while manipulating the device with his right hand, e.g. for setting and/or dispensing of a dose.

A left-handed user typically utilizes such pen-type injectors in a different way. Left-handed users typically hold the device with their right hand while making use of their left hand for dose setting and dose dispensing. With respect to the fixed display orientation of the dose setting dial, a left-handed user is thus compelled to turn over the device for reading the information illustrated in the display window. Hence, utilization of a standard drug delivery device turns out to be quite cumbersome for a left-handed user. As a consequence, left-handed might be exposed to reading errors or misinterpretation of the displayed information. Finally, the patient might be in danger of dispensing an incorrect dose.

A simple solution to this problem could be achieved by manufacturing of different drug delivery devices that are particularly designed for right- and left-handed users. However, production of drug delivery devices of different type and their configuration implies an increase in manufacturing complexity.

SUMMARY

It is therefore an object of the present invention to provide an improved dose display mechanism and a respective drug delivery device that overcome the above-mentioned drawbacks of conventional dose display mechanisms in particular for left-handed users. The present invention therefore aims to provide a dose display mechanism providing unambiguous illustration of dose setting information for both, right-handed and left-handed users. Additionally, the invention focuses on a dose display mechanism that is selectively configurable either for a right-handed or left-handed design of a drug delivery device. Furthermore, the invention aims to simplify construction and assembly of a drug delivery device, in particular of its dose display mechanism.

In a first aspect the present invention provides a dose display mechanism for a drug delivery device that comprises a housing of substantially tubular shape. The housing has at least a first dose displaying window through which dose related information is to be visually displayed. The dose display mechanism further comprises a dose setting dial, preferably of tubular shape, which is rotatably arranged in the housing. The dose setting dial comprises a first and a second dose indicating scale on its peripheral surface. Said dose indicating scales are preferably of helical shape. During a typical dose setting procedure, the dose setting dial is subject to a combined axial and rotational displacement, such that the helically arranged dose-related information is successively illustrated by the fixed displaying window.

The first and the second helical dose indicating scales are particularly adapted to provide an optimized handling of the drug delivery device with respect to right-handed or left-handed usage, respectively. Therefore, the information contents of the first dose indicating scale and the second dose indicating scale are arranged in different orientation, preferably in orientations that are optimized for right-handed use or left-handed use of the dose display mechanism or the drug delivery device.

By providing two dose indicating scales, each of which providing dose-related information in different orientation relative to each other, the dose display mechanism can provide a correct and upright presentation of dose-related information, irrespective on whether the user holds the drug delivery device in a left-handed or right-handed way. Hence, the two dose indicating scales provide a substantially identical information content in a redundant way but in different orientations, each of which being optimized for a right-handed or left-handed user's demands, respectively.

Moreover, by way of providing a first and a second dose indicating scale on a common dose setting dial, the dose display mechanism might become easily configurable or reconfigurable for left-handed or right-handed optimized information content illustration.

Furthermore, the size of the at least first dose displaying window directly matches with the size of the information contents to be displayed by said window. Hence, the dose displaying window provides direct and unaltered visual access to the information contents. The size of the information content and the window size mutually match in order to display the required information in an unequivocal manner. This way, magnifying or other optical display means are generally not required and the housing can be designed in a simple and cost-efficient way. In a preferred approach, the window may comprise a through opening in a side wall section of the housing. Alternatively or additionally, said window may comprise a protective and transparent member covering the information content, wherein the protective member preferably flushes with the outer surface of the housing's side wall section.

In another preferred embodiment, first and second dose indicating scales are axially offset relative to each other. In such configurations, first and second dose indicating scales may be co-aligned in axial direction. Hence, first and second dose indicating scales may be exclusively shifted in axial direction with respect to each other. The first and the second dose indicating scale may present identical information as seen in an axial projection, wherein merely the orientation of digits, numbers or letters of the respective scales differ with respects to each other.

Furthermore, an imaginary line connecting identical information contents of first and second dose indicating scale extends substantially in axial direction as defined by the tubular shape of the housing or the dose setting dial, respectively.

According to a further embodiment of the invention, first and second dose indicating scales are circumferentially offset relative to each other. Hence, an imaginary line connecting identical dose-related information of first and second dose indicating scales extends substantially perpendicular to the axial direction as defined by the tubular shape of the housing or the dose setting dial.

Furthermore and according to another preferred embodiment, it is beneficial, when first and second dose indicating scales are axially and circumferentially offset relative to each other. In such configuration, an imaginary line connecting identical information contents of first and second dose indicating scales extends at an inclination with respect to the axial direction.

In a further preferred embodiment, first and second dose indicating scales present substantially equal information contents. Preferably, each of first and second dose indicating scales comprises a complete set of dose-related information, each of which being entirely informative on the size of a selected dose. This way, first and second dose indicating scales can be regarded as being redundant with respect to each other.

In another beneficial arrangement, the information content of the first dose indicating scale is flipped by approximately 180° relative to the orientation of the information content of the second dose indicating scale. Hence, the first dose indicating scale can be regarded as an upside-down representation of the second dose indicating scale and vice versa. In this way, the first dose indicating scale presents its information content in an upright position when the device is oriented in a typical right-handed fashion. Accordingly, the second dose indicating scale may display its information content in an appropriate and unambiguous way when the drug delivery device is held in a typical left-handed way, e.g. when the drug delivery device is flipped over by 180° compared to its right-handed orientation.

In another preferred aspect, first and second dose indicating scales extent along parallel helices on the common dose setting dial. Hence, first and second dose indication scales comprise the same sense of rotation.

Accordingly, first and second dose indicating scales feature the same graduation of display units, wherein merely the orientation of the respective information representation preferably varies by 180°.

According to a further preferred embodiment of the invention, the display window of the housing comprises first and second adjacently arranged display sections. Hence, the display window is divided into different display sections, which may be located axially next to one another. Here, the first display section overlaps with the first dose indicating scale and the second display section preferably overlaps with the second dose indicating scale. By further providing a cover element adapted to selectively cover the first or the second display section, the dose display mechanism and the entire drug delivery device can be selectively switched to a left-handed or right-handed configuration, simply by arranging the cover element over the first or second display section, respectively.

In another preferred embodiment, the housing comprises an additional, second display window, which is axially and/or circumferentially offset from the first display window. Also here, first and second display windows substantially overlap with first and second dose indicating scales of the dose setting dial, respectively. Having two display windows, the dose display mechanism is generally adapted to simultaneously provide redundant dose-related information, which is correctly illustrated in a right-handed as well as in a left-handed orientation of the drug delivery device, respectively.

Depending on axial and circumferential offset of first and second dose indicating scales, also the respective display windows are arranged with a respective axial and/or circumferential offset relative to each other. It is further conceivable, that first and second display windows substantially overlap in an axial or circumferential projection, wherein an imaginary line connecting first and second display windows extents substantially in axial direction or perpendicular thereto.

However, if first and second dose indicating scales are axially and circumferentially offset relative to each other, this will also apply to the respective first and second display windows.

In a further preferable embodiment, first and second display windows are offset in circumferential direction relative to each other by substantially 180°. Hence, first and second display windows are diametrically opposed to each other in the tubular shaped housing's sidewall.

According to another independent aspect, the invention also relates to a drive mechanism for a drug delivery device that comprises a dose display mechanism according to the present invention.

Also, the present invention refers to a respective drug delivery device for dispensing of a pre-defined dose of a medicinal product and which further comprises the present dose display mechanism.

Furthermore, and according to another preferred embodiment, the drug delivery device comprises a cartridge filled with the medicinal product. The device may be of reusable and/or disposable type. Preferably, the device is to be commercially distributed with a filled cartridge readily disposed therein.

The term "medicament" or "medicinal product", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(0)14 Asp28 Pro36, Pro37, Pro38 Exendin-4(1-39)-NH2,
H-(Lys)6-desPro36, Pro37, Pro38 [Met(0)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(02)25, Asp28] Exendin-4(1-39)-Lys6-NH2,
H-des Asp28 Pro36, Pro37, Pro38 [Met(O)14, Trp(02)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(02)25, Asp28] Exendin-4(1-39)-NH2,
des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(02)25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be apparent to those skilled in the pertinent art that various modifications and variations can be made to the present invention without departing from the spirit and scope of the invention. Further, it is to be noted, that any reference signs used in the appended claims are not to be construed as limiting the scope of the present invention.

BRIEF DESCRIPTION OF THE DRAWINGS

Without limitation, the present invention will be explained in greater detail below in connection with preferred embodiments and with reference to the drawings in which:

FIG. 4 is illustrative of another embodiment, wherein the housing comprises a single display window divided into axially adjacently arranged display sections, FIG. 5 shows the display mechanism according to FIG. 4, wherein only the first dose indicating scale is visible and FIG. 6 illustrates a configuration, wherein only the second dose indicating scale is visible, FIG. 9 shows an unrolled dose setting dial applicable with the housing as illustrated in FIG. 8.

DETAILED DESCRIPTION

Figure 1:
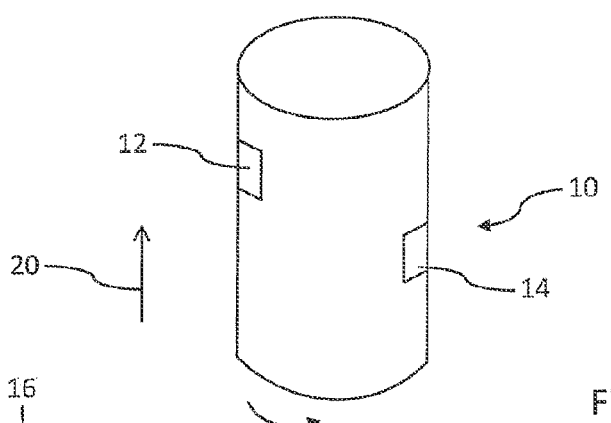
FIG. 1 schematically illustrates a housing of a dose display mechanism that comprises two dose displaying windows, FIG. 2 schematically shows an unrolled dose setting dial to be used in conjunction with the housing illustrated in FIG. 1.

FIG. 1 schematically illustrates a dose display mechanism having a housing 10 that comprises a first and a second dose displaying window 12, 14. The housing 10 is of substantially tubular shape. Its cylinder long axis extents along an axial direction 20 and its peripheral wall substantially follows a circumferential direction 22 being substantially perpendicular to the elongation of axes 20.

The displaying windows 12, 14 may comprise any suitable opening in the housing. In a rather simple embodiment, the windows 12, 14 merely comprise a hole or a through opening in the housing. In other embodiments, the displaying windows 12, 14 may comprise a transparent cover that allows to visualize and to display the actual device configuration. Typically, the displaying windows 12, 14 are adapted to provide dose-related information by displaying numerical and/or graphical symbols, such as digits, numbers or other suitable characters.

Figure 2:
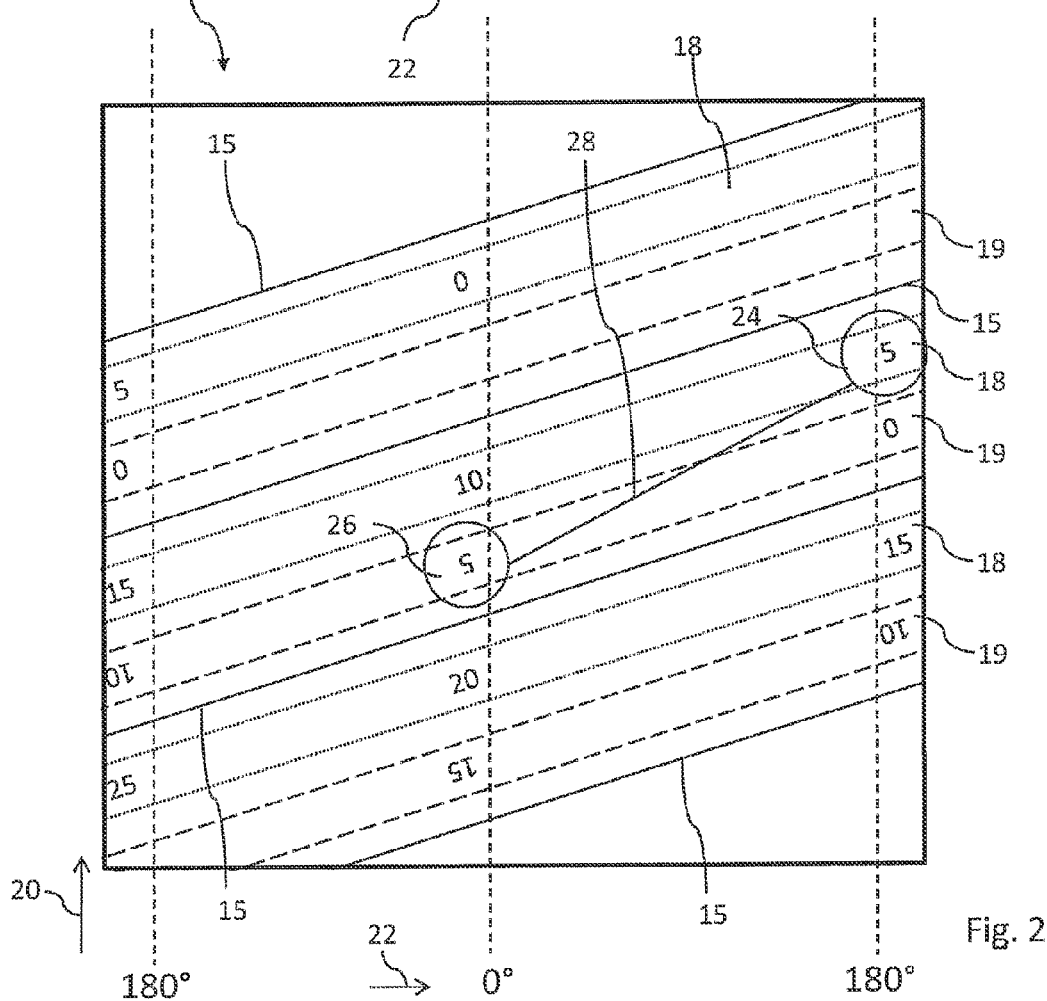
Figure 3:
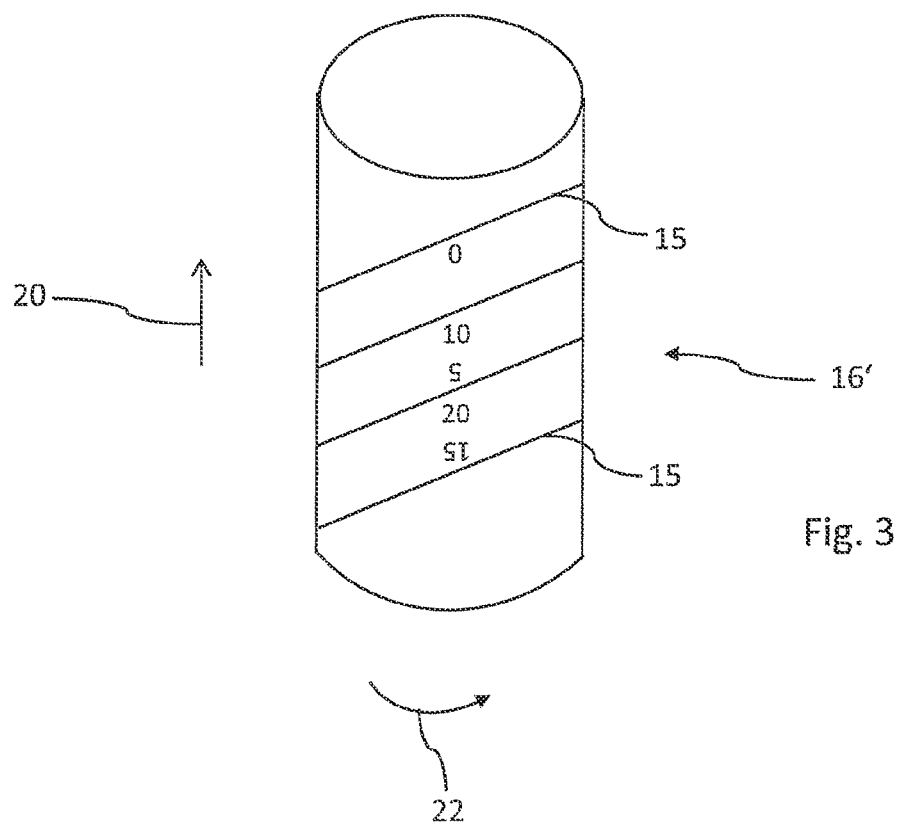
FIG. 3 shows the dose setting dial according to FIG. 2 in a cylindrically rolled up configuration.

Inside the housing 10, there is arranged a tubular shaped dose setting dial 16, which is exemplary illustrated in FIG. 2 in an unrolled state. FIG. 3 shows the respective dose setting dial 16' in its rolled up tubular shape.

As can be seen from FIG. 2, the dose setting dial comprises a first and a second helical dose indicating scale 18, 19. Said scales 18, 19 are axially and circumferentially offset relative to each other. As further indicated by the helical thread 15, the dose setting dial is typically subject to a combined axial and circumferential displacement relative to the housing 10 during a dose setting procedure. The first and the second dose indicating scales 18, 19 extend parallel with respect to each other. Both dose indicating scales 18, 19 comprise the same information contents, typically displaying a regular and equidistant graduation of incrementing numbers.

The two dose indicating scales 18, 19 are readable from different device orientations, respectively. For reading the first dose indicating scale 18, the dose setting dial 16 or the respective drug delivery device should be kept in an upright orientation. For reading of the second dose indicating scale 19, the dose setting dial has to be rotated by 180°. Hence, the device has to be held upside-down, which for the given type of device is typical for a left-handed user.

Orientation of the information content, hence the presentation of the respective numbers or symbols of each dose indicating scale differs by substantially 180°. The axial and circumferential offset of first and second dose indicating scales 18, 19 corresponds to the respective axial and circumferential offset of first and second displaying windows 12, 14 of the housing 10. In this way, the illustrated dose display mechanism 10 is adapted to show identical dose-related information in both windows 12, 14 simultaneously in different, typically flipped orientations. In this way, the display mechanism and a respectively equipped drug delivery device is universally applicable for both, right-handed and left-handed users.

As further illustrated in FIG. 2 a digit 24 of the first dose indicating scale 18 is circumferentially offset to the identical digit 26 of the second dose indicating scale 19. The two digits 24, 26, hence, their corresponding dose indicating scales 18, 19 are circumferentially offset by 180°. In the embodiment according to FIGS. 1 to 3, the digit 24 appears at the position of the first window 12 when the digit 26 of the second dose indicating scale simultaneously appears at the displaying window 14.

As further illustrated, an imaginary connection line 28 connecting identical digits 24, 26 of first and second dose indicating scales 18, 19 extends at an inclination with respect to the longitudinal axes 20 as well as with respect to the circumferential direction 22.

Figure 7:
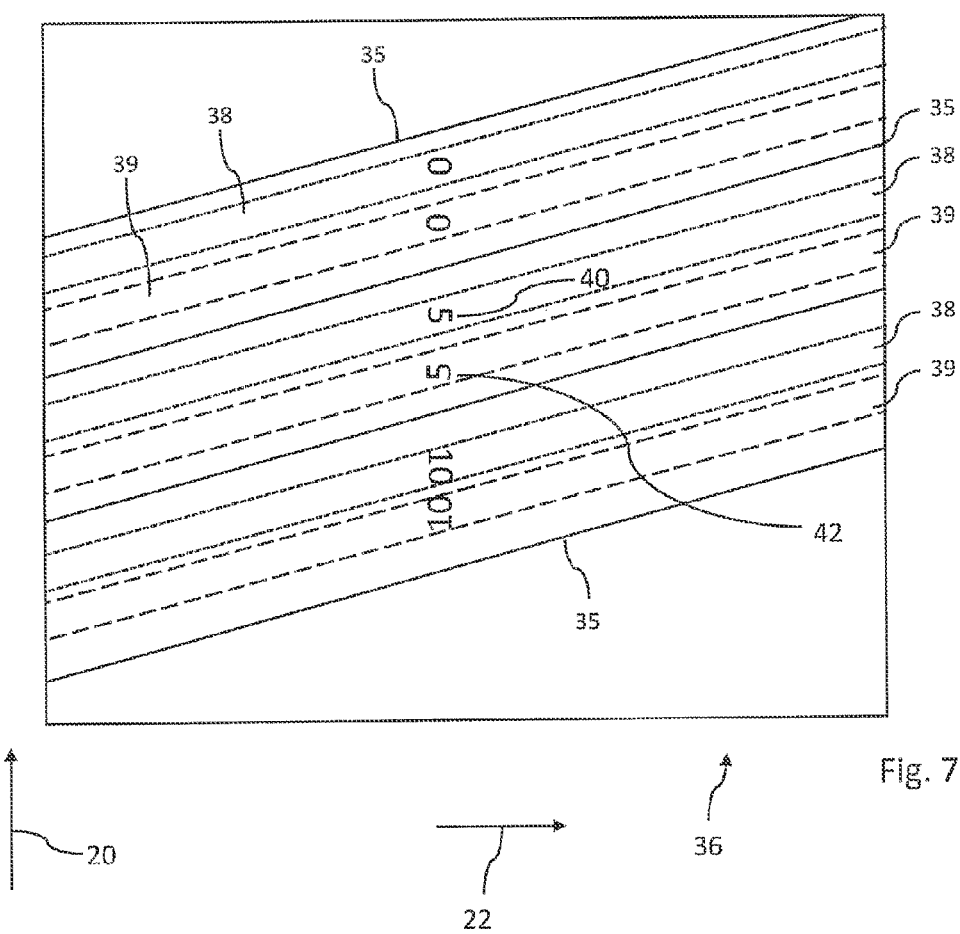
FIG. 7 is illustrative of an unrolled dose setting dial being applicable with any one of the housings as illustrated through FIGS. 4 to 6, FIG. 8 schematically illustrates another dose display mechanism having a housing with first and second axially overlapping but circumferentially shifted displaying windows

In the embodiment according to FIGS. 4 to 7, the housing 30 comprises a single dose displaying window 32, which is divided in first and second display sections 33, 34. Here, the first display section 33 is arranged in an overlapping way with a corresponding first indicating scale 38 as illustrated in FIG. 7. Correspondingly, the second display section 34 overlaps with a respective second dose indicating scale 39. Depending on whether the dose display mechanism or the correspondingly equipped drug delivery device is intended for right-handed or left-handed use, respectively, an appropriate cover element 37 can be used to cover one of said display sections 33, 34.

The cover element 37 may either permanently or re-configurably attached to the respective display sections 33, 34. In this way, a respective dose display mechanism can be configured or even re-configured for the purpose of right-handed or left-handed usage.

Since first and second display sections 33, 34 of the display window 32 substantially overlap in circumferential projection but are located axially next to one another, the dose setting dial 36 as shown in FIG. 7 comprises a different configuration compared to the dose setting dial 16 as illustrated in FIG. 2. As can be seen from its unrolled configuration, the dose setting dial 36 also comprises two parallel oriented but inclined or helically extending dose indicating scales 38, 39. Here, the numbers 40, 42 of said scales 38, 39 are upside-down with respect to each other. Appropriate reading of number 40 requires a counter clockwise rotation of 90°, whereas proper reading of a digit 42 of the other dose indicating scale 39 requires clockwise rotation by 90°.

In contrast to the dose setting dial 16 of FIG. 2, the dose setting dial 36 as illustrated in FIG. 7 comprises first and second dose indicating scales 38, 39 that are merely offset in axial direction with respect to each other. As can be seen from FIG. 7, identical numbers of first and second dose indicating scales 38, 39 axially overlap. Correspondingly, a not further illustrated imaginary line connecting identical numbers 40, 42 of first and second dose indicating scales 38, 39 substantially extends in axial direction.

Also here, the dose setting dial 36 comprises a helical thread 35 optionally providing a threaded engagement of housing 30 and dose setting dial 36. By means of such a screw structure, the dose setting dial is allowed to rotatably move towards a proximal end of the drug delivery device during dose setting.

In a third embodiment according to FIGS. 8 and 9, the housing 50 also comprises two diametrically opposed displaying windows 52, 54. But here, the displaying windows 52, 54 axially overlap. They are typically circumferentially offset by about 180°. As further illustrated in FIG. 9, the respective dose setting dial 56 comprises two parallel oriented helical extending dose indicating scales 58, 59, each of which comprising substantially the same information content in form of graduated display units that are in turn represented by numbers 60, 62.

Comparable to the dose setting dials 16, 36 also the dose setting dial 56 comprises a helical thread 55 indicating the helical-like motion of the dial 56 relative to the housing 50 during a dose setting procedure. Since the first and second displaying windows 52, 54 are merely circumferentially offset with respect to each other, the same applies to the corresponding dose indicating scales 58, 59. In the illustration of FIG. 9, the imaginary position of first and second displaying windows 52, 54 is illustrated, each of which simultaneously displaying the same number 60, 62, but represented in different orientations, that are flipped by 180° with respect to each other.

Generally, the dose setting dial may be releasably connected to a not further illustrated drive mechanism of a drug delivery device, typically by some clutch means. For setting of the dose, the dose setting dial may be rotated together with an inner cylinder or a comparable component of the drive mechanism. Typically, during dose dispensing, the clutch means may disengage the dose setting dial from the drive mechanism. Further, the dose setting dial may comprise one or more stops to limit the maximum amount of a single dose.

The invention claimed is:

1. A dose display mechanism for a drug delivery device, the dose display mechanism comprising:
    a housing of substantially tubular shape and having a first dose displaying window,
    a dose setting dial rotatably arranged in the housing and comprising a first helically extending dose indicating scale and a second helically extending dose indicating scale on its peripheral surface,
    wherein the first helical dose indicating scale has a first information content and the second helical dose indicating scale has a second information content, wherein the first and the second information contents are arranged in different orientations, and wherein a size of the first dose displaying window directly matches with a size of the first information content, and
    wherein the housing comprises a second dose displaying window axially and/or circumferentially offset from the first dose displaying window, and wherein the first and the second dose displaying windows substantially overlap with the first and the second helical dose indicating scales, respectively.

2. The dose display mechanism according to claim 1, wherein the first and the second helical dose indicating scales are axially offset relative to each other.

3. The dose display mechanism according to claim 1, wherein the first and the second helical dose indicating scales are circumferentially offset relative to each other.

4. The dose display mechanism according to claim 1, wherein the first and the second information are substantially equal.

5. The dose display mechanism according to claim 1, wherein the first information content is flipped by approximately 180° relative to the orientation of the second information content.

6. The dose display mechanism according to claim 1, wherein the first and the second helical dose indicating scales extend along parallel helices on the dose setting dial.

7. The dose display mechanism according to claim 1, wherein a graduation of the first helical dose indicating scale and a graduation of the second helical dose indicating scale extend in the same direction.

8. The dose display mechanism according to claim 1, wherein the first dose displaying window comprises first and second adjacently arranged display sections, wherein the first display section overlaps with the first helical dose indicating scale and wherein the second display section overlaps with the second helical dose indicating scale.

9. The dose display mechanism according to claim 8, further comprising a cover element adapted to selectively cover the first or the second display section, respectively.

10. The dose display mechanism according to claim 1, wherein the first and the second dose displaying windows are offset in circumferential direction relative to each other by substantially 180°.

11. The dose display mechanism according to claim 1, wherein the first and the second dose displaying windows are axially and circumferentially offset.

12. A drug delivery device for dispensing of a pre-defined dose of a medicinal product, being selectively configurable for left- and right-handed users and comprising:
   the dose display mechanism according to claim 1; and
   a cartridge filled with the medicinal product.

* * * * *